US012648796B2

(12) United States Patent　　　　　　(10) Patent No.:　US 12,648,796 B2
Truckai et al.　　　　　　　　　　　　(45) Date of Patent:　　　Jun. 9, 2026

(54) MEDICAL ROBOTIC SYSTEMS AND METHODS

(71) Applicant: Meditrina, Inc., San Jose, CA (US)

(72) Inventors: Csaba Truckai, Saratoga, CA (US); Matt Williams, Walnut Creek, CA (US); Alan De Lira, Daly City, CA (US)

(73) Assignee: Meditrina, Inc., San Jose, CA (US)

( * ) Notice: Subject to any disclaimer, the term of this patent is extended or adjusted under 35 U.S.C. 154(b) by 48 days.

(21) Appl. No.: 18/517,522

(22) Filed: Nov. 22, 2023

(65) Prior Publication Data

US 2024/0173087 A1　　May 30, 2024

Related U.S. Application Data

(60) Provisional application No. 63/385,189, filed on Nov. 28, 2022.

(51) Int. Cl.
　*A61B 17/42*　　　(2006.01)
　*A61B 8/00*　　　(2006.01)
　*A61B 8/12*　　　(2006.01)
　*A61B 17/3205*　　(2006.01)
　*A61B 34/30*　　　(2016.01)
(52) U.S. Cl.
　CPC ............ *A61B 17/4241* (2013.01); *A61B 8/12* (2013.01); *A61B 8/4218* (2013.01); *A61B 17/3205* (2013.01); *A61B 17/42* (2013.01);
*A61B 34/30* (2016.02); *A61B 2017/4216* (2013.01); *A61B 2034/302* (2016.02); *A61B 2034/303* (2016.02)

(58) Field of Classification Search
CPC ..... A61B 34/30; A61B 17/42; A61B 17/4241; A61B 2017/4225; A61B 2017/4216
See application file for complete search history.

(56) References Cited

U.S. PATENT DOCUMENTS

| | | | |
|---|---|---|---|
| 8,545,513 B2 | 10/2013 | Blair et al. | |
| 10,433,717 B1 | 10/2019 | Truckai et al. | |
| 10,695,092 B2 | 6/2020 | Wu et al. | |
| 10,881,432 B1 | 1/2021 | Leal et al. | |
| 11,259,695 B2 | 3/2022 | Truckai et al. | |
| 2012/0323079 A1 | 12/2012 | Bakare et al. | |
| 2013/0131459 A1* | 5/2013 | Williams | A61B 1/06 600/249 |
| 2019/0104932 A1* | 4/2019 | Truckai | A61B 17/320016 |
| 2020/0268440 A1* | 8/2020 | Bergeron | A61B 34/37 |
| 2021/0361272 A1 | 11/2021 | Nakajima et al. | |
| 2023/0076736 A1* | 3/2023 | Scheib | A61B 17/4241 |

OTHER PUBLICATIONS

US 5,832,252, 1/1995, Failla et al. (withdrawn)

\* cited by examiner

*Primary Examiner* — Sarah A Long
(74) *Attorney, Agent, or Firm* — Levine Bagade Han LLP

(57) ABSTRACT

Robotic surgical systems and methods for using both laparoscopic and trans-cervical tools and imaging devices to resect fibroids or other abnormal uterine tissue.

10 Claims, 10 Drawing Sheets

MEDICAL ROBOTIC SYSTEMS AND METHODS

BACKGROUND

The present invention is related to robotic surgical systems and methods for using both laparoscopic and trans-cervical tools and imaging devices to resect fibroids or other abnormal uterine tissue.

SUMMARY

The principles of the present disclosure relate to medical robotic systems. For example, some aspects of the techniques described herein relate to medical robot systems including both laparoscopic and trans-cervical robotic arms each having a plurality of moveable arm segments; endoscopic viewing assemblies detachably coupled to a distal segment of such robotic arms, a stabilizing device detachably coupled to a distal segment of a robotic arm for stabilizing a cervix, and elongate tools carrying ultrasound transducers for imaging a fibroid in the patient's uterus.

Variations of a medical robot system further include motor drives configured to manipulate various implements coupled to the robotic arms. For example, such motor drives can rotate or axially move the elongate endoscope shafts or other tools relative to a longitudinal axis.

Motor drives of the present robotic system can be configured to rotate a tool shaft relative to its longitudinal axis and/or move the tool shaft axially relative to its longitudinal axis. Examples of such treatment tools include, but are not limited to an endoscope, a retraction device, an ultrasound device, a resecting device, a cervical stabilizing device, an intra-uterine manipulation device, an injection device for injecting a tissue adhesive, a coagulation device, and a biopsy device.

In additional variations, a treatment tool includes a resecting device with a moving cutting member, and wherein the system includes a resecting motor drive for moving the cutting member at least rotationally and also axially.

In some aspects, the techniques described herein relate to a method of treating or resecting tissue in a patient's uterine cavity, including: providing a medical robot system with a plurality of robotic arms each having a plurality of moveable arm segments with one arm carrying a plurality of motor drives for moving an endoscope and a resecting device trans-cervically and a second arm the distal arm segment, with another one arm adapted to carry an endoscope and an ultrasound device for laparoscopic introduction; where the working end of the resecting device is introduced trans-cervically into the patient's uterine cavity to resect tissue, and the ultrasound device is adapted to provide ultrasound images of the targeted tissue in real-time, and; and a controller operates the plurality of motor drives to move the working end of the resecting device in a predetermined pattern to resect tissue responsive to parameters determined by the ultrasound images.

The methods disclosed herein can further include a controller that operates a motor drive to move the cutter of a resecting device in an axial pattern while actuating the cutter to resect tissue. In addition, the controller can operate a motor drive to move the cutter in a rotational or angular pattern while actuating the cutter to resect tissue.

The present disclosure is related to commonly assigned U.S. patent application Ser. No. 17/662,182, the entirety of which is incorporated by reference.

BRIEF DESCRIPTION OF DRAWINGS

Additional aspects of the invention will become clear from the following description of illustrative embodiments and from the attached drawings in which.

DETAILED DESCRIPTION

Figure 1A:
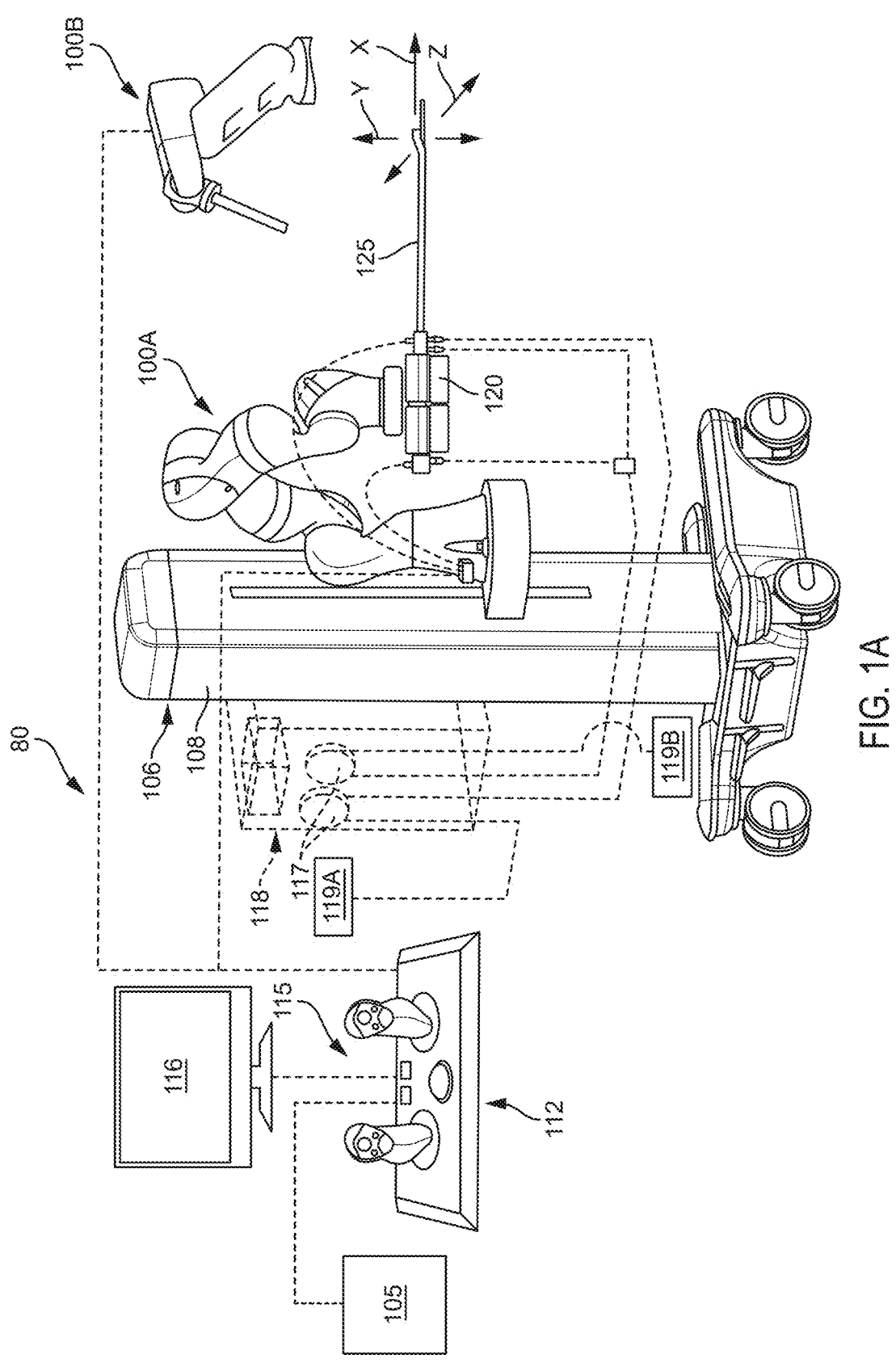
FIG. 1A is an illustration of a surgical robotic system, including a roll stand with a tower portion, a surgical console and a controller, a user input interface, a first robotic arm adapted to carry trans-cervically introduce tools to treat intrauterine tissues, and a second robotic arm to introduce tools laparoscopically.
Figure 1B:
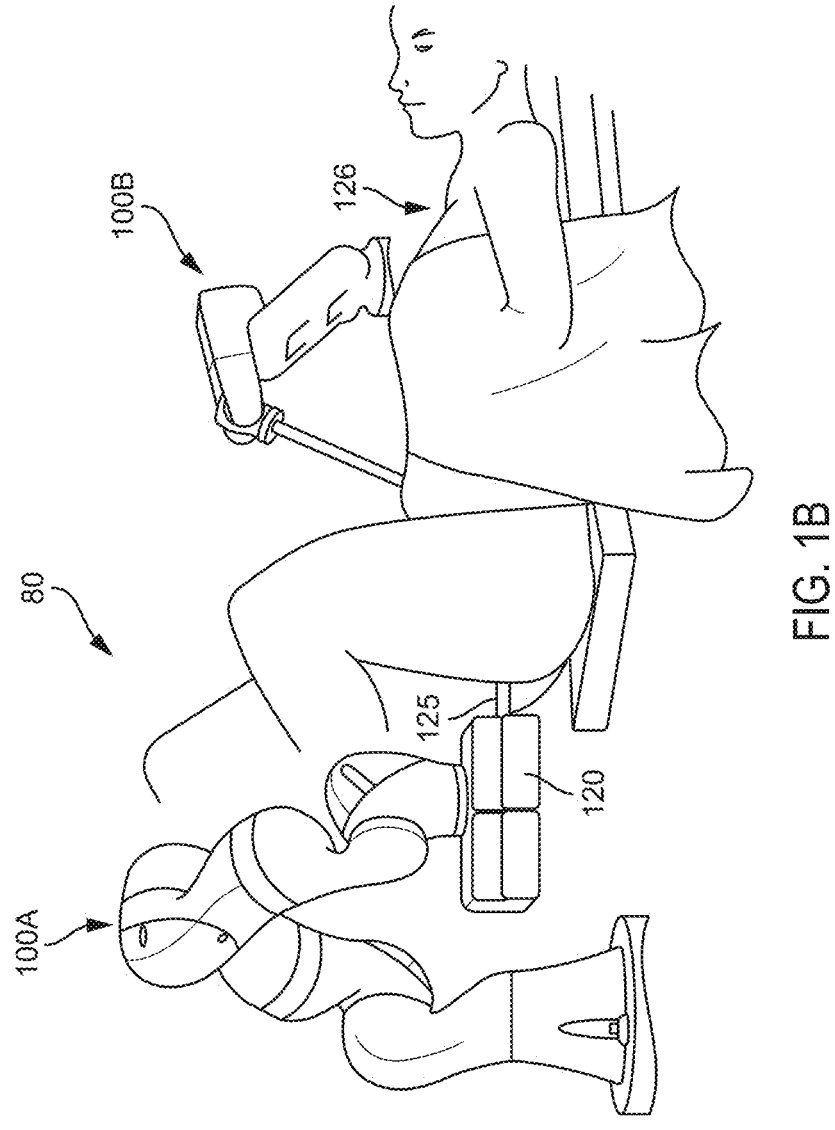
FIG. 1B is a view of the first and second robotic arms shown introducing tools into a patient's body trans-cervically and laparoscopically.

FIGS. 1A and 1B illustrate a surgical system 80 with a first multi-link robotic arm 100A and a second multi-link 100B arm, wherein the arms 100A and 100B (see FIG. 1B) are interconnected with a controller 105 that is configured to control or monitor the positions of each arm. The dual arms are adapted for use in gynecology procedures or other procedures in which a combination of natural orifice access and laparoscopic access are used.

In FIG. 1A, the first arm 100A is shown, which includes a roll stand 106 with a vertical column or tower 108 that carries the robotic arm 100A that is operated from a console 112 with user input interface 115 and image display or monitor 116. The user input interface 115 can comprise one or more joysticks, rollerballs, and other input mechanisms known in the art. The display 116 may be a touch screen that can further be used to direct movement of the arm 100A and or arm 100B and/or control other operating parameters of the system as described below. The robotic arm 100A is capable of movement relative to multiple axes as provided by multiple drives and actuators. In one variation, the robotic arm 100A of the system can comprise a commercially available, multiple-segment robotic arm manufactured by KUKA Robotics Corporation, having an office at 51870 Shelby Parkway, Shelby Township, Michigan, 48315.

FIG. 1A further shows a fluid management system 118, as known in the art, and which is carried by the system 80. The first and second arms 100A, 100B, fluid management system 118 and peristaltic pump 117 therein, and tools described below are all operatively coupled to the controller 105. The fluid management system has a fluid source 119A such a saline bags and a fluid collection reservoir 119B as shown in FIG. 1A.

Figure 2:
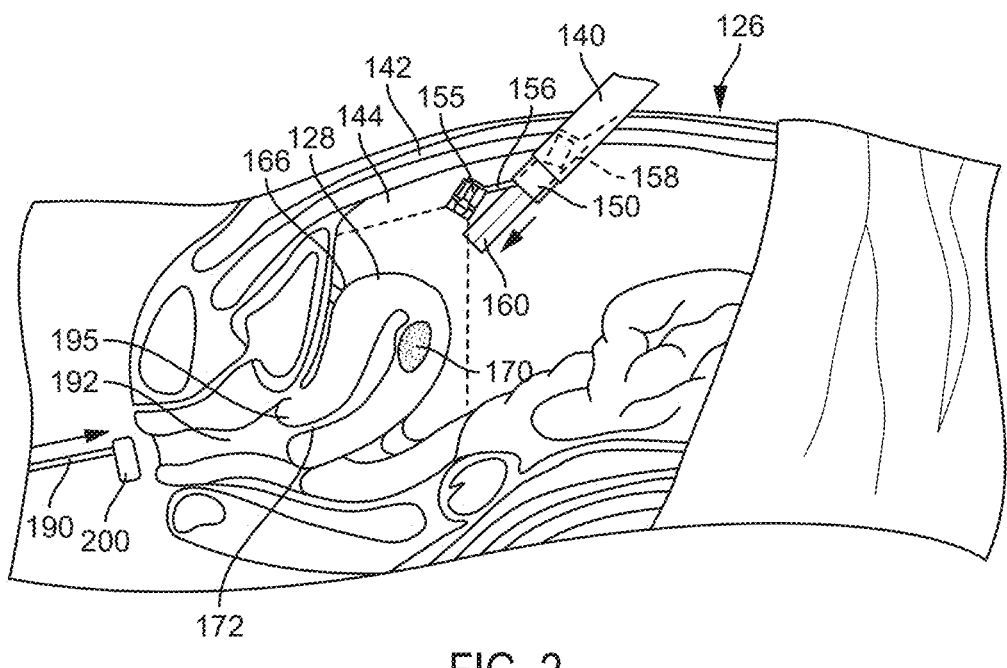
FIG. 2 is a schematic sectional view of the patient's body in an initial step of a method of the invention showing the laparoscopic introduction of a tool comprising an endoscope into the patient's insufflated abdominal cavity.

Referring to FIG. 1A, the moveable base and arm segments of the arm 100A are motor-driven to allow a drive assembly 120 and tool shaft such as endoscope 125 to move in all directions (pitch, yaw, etc.) as in directions X, Y, and Z to access to the patient's body 126 (FIG. 1B). A as shown in FIGS. 1A and 1B, the drive assembly 120 can be adapted to carry multiple tool drives for multiple tools that are configured for trans-vaginal introduction and trans-cervical introduction into a patient's uterus 128 (FIG. 2). As will be described below, single-use surgical tools are adapted for detachable coupling to the drive assembly 120. Several types of tools may be coupled to the drive assembly 120, including (i) a cervical stabilization device, (ii) an ultrasound device, (iii) a uterine manipulation device for repositioning the uterus, (iv) an endoscope 125, (v) a resecting device, (vi) a polyp retraction device, and (vii) a tool to introduce and apply tissue adhesives to a targeted site, which are described further below.

Referring again to FIG. 1B, the second multi-segment arm 100B also has multiple arm segments providing for multiple directions of freedom of movement and is configured for use in laparoscopically introducing at least one tool through a port or cannula 140 in the patient's abdominal wall 142 into the abdominal cavity 144 such as an endoscope 150 for viewing the exterior of the patient's uterus 128 (FIG. 2). The second arm 100B can comprise a motorized, fully robotic arm or the arm 100B can comprise a type of arm that can be moved manually and manipulated in multiple degrees of freedom and then locked in a final selected position following access to the patient's abdominal cavity 144. The tools that may be carried by the second arm 100B can include (i) an endoscope 150, (ii) a uterine grasper or other forms of manipulation device that can be used to either grasp, move or manipulate the position of the patient's uterus, (iii) a tool for positioning an ultrasound transducer against the exterior of the uterus, and (iv) a tool to introduce and apply tissue adhesives to a targeted site.

Figure 3:
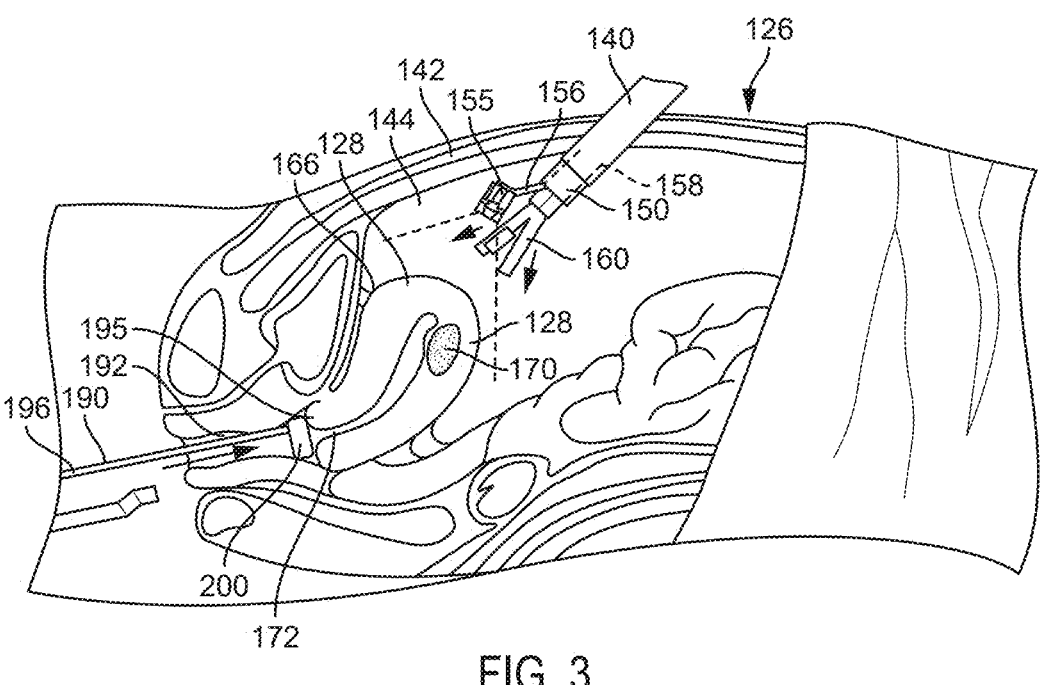
FIG. 3 illustrates a subsequent step in the method where a grasping tool is introduced through our working channel in the endoscope under microscopic vision, and a cervical stabilization tool is introduced through the patient's vagina to engage the cervix.
Figures 9A, 9B:
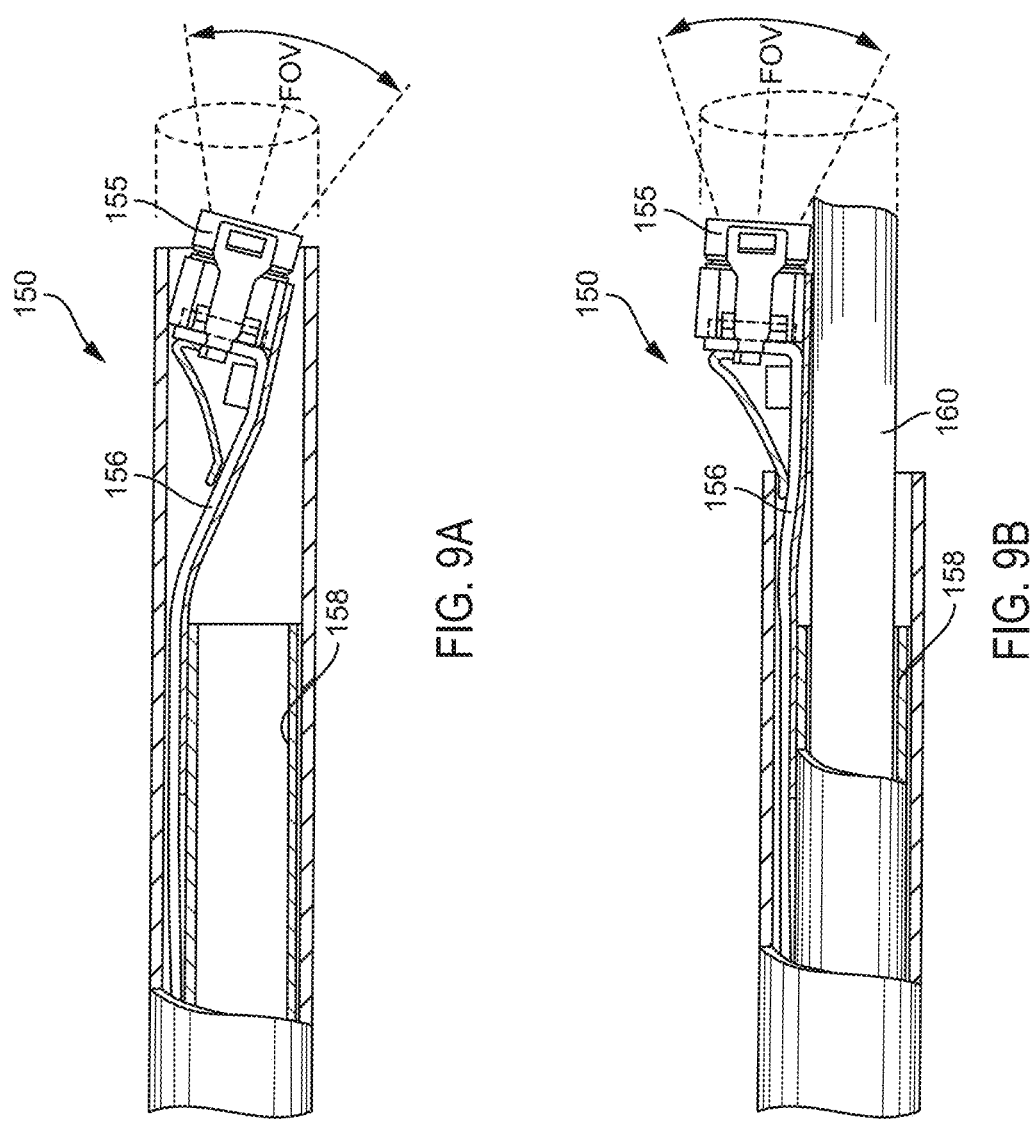
FIG. 9A is a cut-away view of a distal end of the laparoscopic endoscope of FIGS. 2 to 5 with the image sensor retracted into the endoscope shaft prior to deployment.
FIG. 9B is another cut-away view of the distal end of the laparoscopic endoscope of FIG. 9A with the image sensor deployed as shown in FIGS. 2 to 5.

Now referring to FIG. 2, a schematic sectional view of the patient 126 is shown in order to describe a method of the invention which includes (i) introducing at least one tool into a patient's uterus 128 through natural orifices (i.e., a patient's vagina and cervical canal) and (ii) contemporaneously introducing at least one tool laparoscopically into a patient's abdominal cavity 144 to observe, image, manipulate or treaty the uterus 128 from an exterior thereof. In FIG. 2, it can be understood that an access port or cannula 140 can be provided in the patient's abdominal wall 142, as is accomplished using a Veress needle for insufflation, a trocar, and canula as is known in the art. Thereafter, an elongated endoscope 150 is inserted through the cannula 140 where the distal end of the endoscope carries an image sensor 155 on a deflectable member 156 as disclosed in commonly-owned U.S. Pat. No. 11,259,695 and shown in FIGS. 9A-9B below. The shaft of endoscope 150 has a large working channel 158 therein, which allows for an additional tool 160 to be introduced through the working channel 158. FIGS. 2 and 3 illustrate a grasper-type tool or manipulation tool 160 being introduced through the working channel 158.

Figure 4:
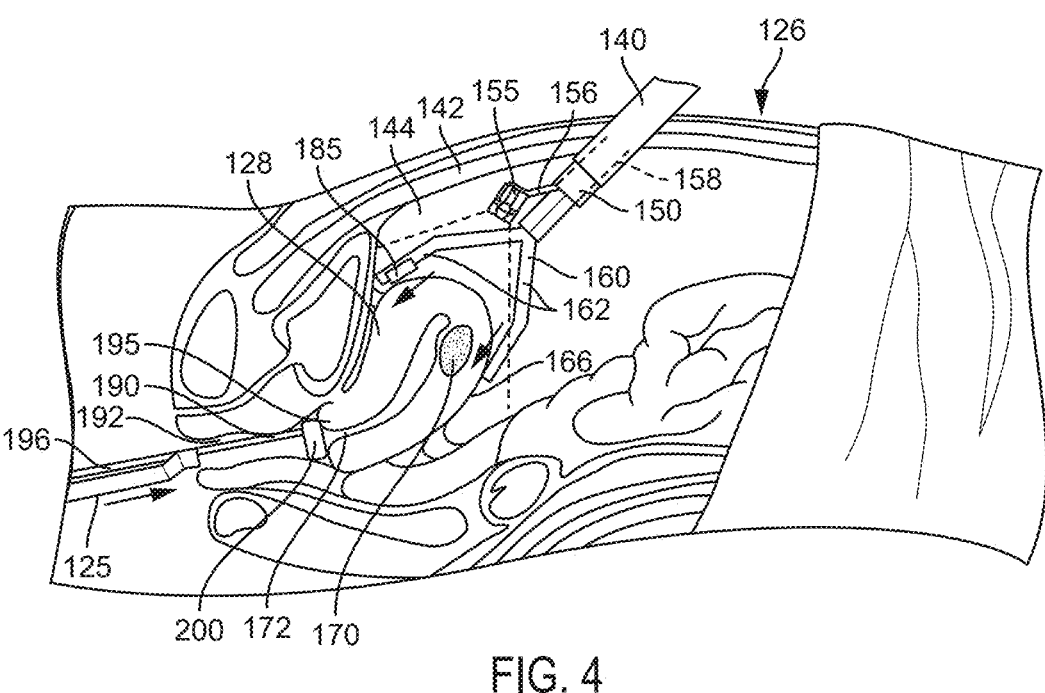
FIG. 4 illustrates a subsequent step in the method where jaws of the grasping tool are further expanded to grasp the uterus and mobilize the uterus. At the same time, an endoscope is introduced into the patient's vagina.

In FIGS. 3 and 4, further steps of the method of the invention are shown, where FIG. 3 shows the jaws 162 of the tool 160 can be used to bluntly dissect around the surface or serosa 166 of the uterus 128 as well as using the jaws 162 to clamp onto to and mobilize the uterus 128. In one aspect of the method, the grasper or manipulation tool 160 is adapted for moving the uterus 128 in such a way that targeted tissue, such as a fibroid 170 in the uterus 128, is aligned with the axis of the patient's cervical canal 172 so that an endoscope 125 introduced through the patient's cervical canal 172 can be navigated directly to fibroid 170 to allow a rigid-shaft resecting device 180 to be aligned with the fibroid 170.

FIG. 4 further illustrates that at least one jaw 162 of the grasper tool 160 carries at least one ultrasound sensor 185 that is pressed into contact with the serosa 166 of the uterus 128 as the jaws 162 are closed. The ultrasound transducer or transducers are capable of propagating acoustic waves 188 in the uterus 128 for imaging the targeted fibroid 170. The ultrasound transducers are adapted to send signals to the controller 105, and a processor then can generate and display the ultrasound images on the image display 116 (FIG. 1A). In this variation, the grasper tool 160 is used to position the uterus 128 in alignment the cervical canal 172 and also positions the uterus 128 such that it is surrounded by insufflation gas in the insufflated abdominal cavity 144, which provided more defined ultrasound imaged since the gas surrounding the uterus 128 does not propagate acoustic waves to provide the clear definition of the serosa 166 on the image display or monitor 116.

Figure 7:
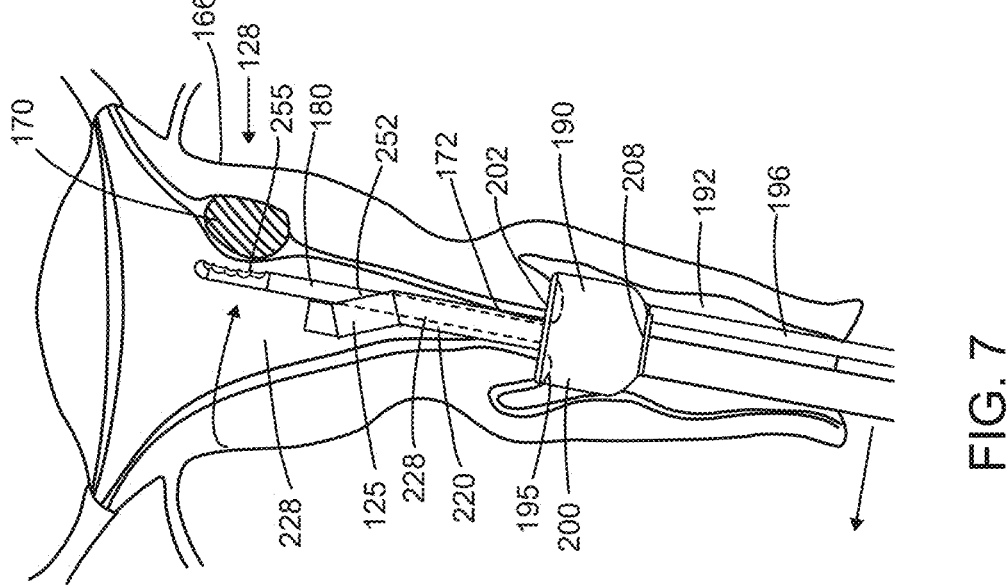
FIGS. 6 and 7 are enlarged views of an elongated shaft and a working end of a cervical stabilization device.
Figure 6:
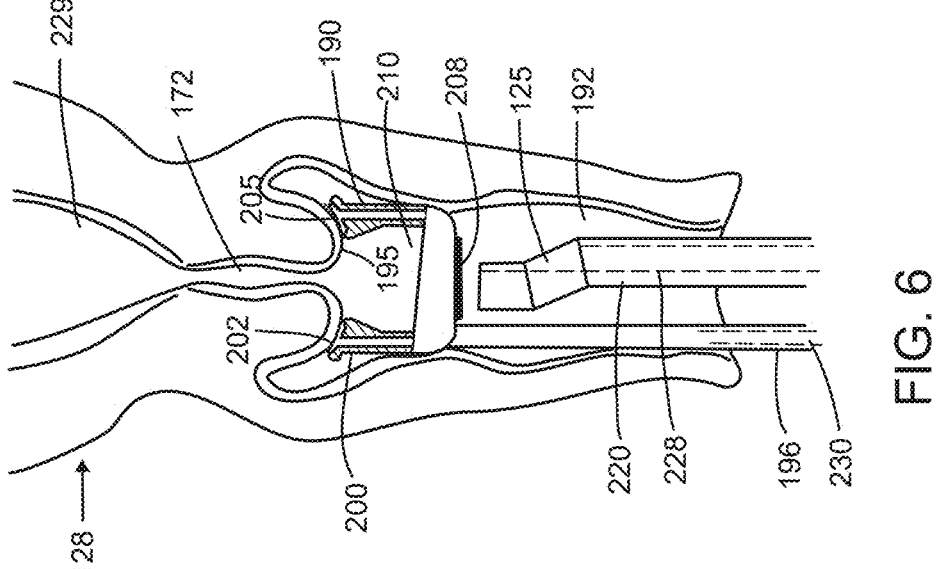

Now referring back to FIGS. 1B and 2, it can be seen that the first robotic arms 100A are operating to introduce a cervical stabilizing device 190 through the patient's vagina 192 to engage the exterior of the cervix 195. FIGS. 6 and 7 are enlarged views of the elongated shaft 196 and working end of the cervical stabilization device 190. The working end comprises an annular member 200 with an engagement surface 202 (see FIG. 6) configured with a suction port or ports 205 that are adapted to suction the cervix 195 into contact with the device 190 (FIGS. 6-7). As can be seen in FIGS. 6 and 7, the working end of the stabilization device 195 has an access port 208 with a seal for introduction of the endoscope 125 or another tool into the patient's cervical canal 172. The annular member 200 of the cervical stabilizer 190 also is adapted to collect fluid discharge in chamber 210 (FIG. 6) from the patient's uterine cavity 28 and cervical canal 172 that may escape around the endoscope shaft. Such a fluid discharge is removed from the annular member 200 and chamber 210 by a negative pressure source (outflow peristaltic pump 177) of the fluid management system 118 with the collected fluid weighed to assist in fluid deficit calculation as is known in the art (FIG. 1A). The negative pressure source or pump 177 communicates with a passageway 230 in the elongated shaft 196. It should be further appreciated that the working end of such a stabilization device 190 can also carry an ultrasound transducer for imaging mentioned the uterus 128 from the angle of the cervix (not shown).

Figure 8A:
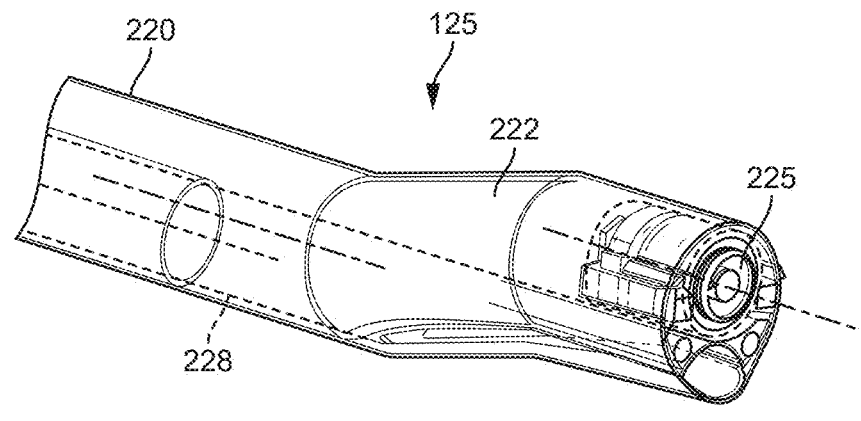
FIG. 8A is a perspective view of the distal end of the trans-cervical endoscope of the type shown in FIGS. 4 to 7 with a collapsed working channel.
Figure 8B:
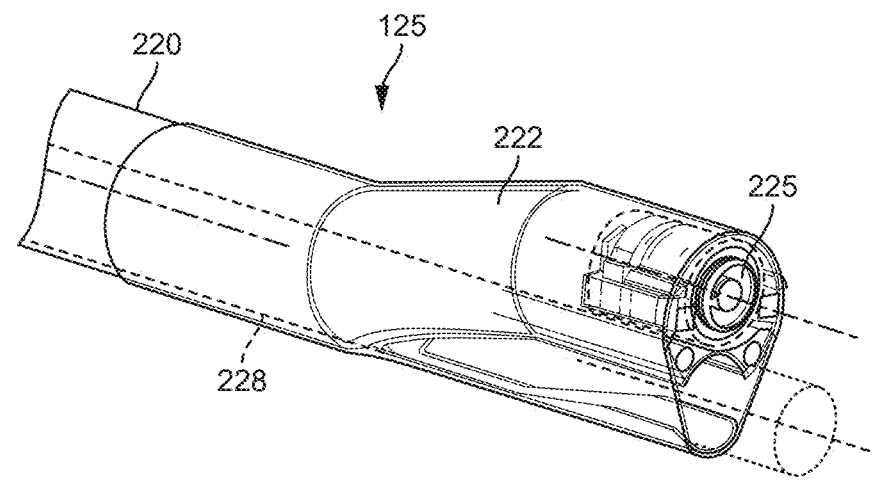
FIG. 8B is another view of the distal end of the trans-cervical endoscope of FIG. 8A with a resecting device introduced through the working channel, as shown in FIGS. 5 and 7.

FIG. 3 shows the cervical stabilizer 190 after being introduced through the vagina 192 to engage the cervix 195. FIG. 4 shows the endoscope 125 introduced through the access port 208 in the annular member 200 and FIG. 5 then shows the endoscope 125 advanced into the uterine cavity. The endoscope 125 is of the type disclosed in commonly-owned U.S. Pat. No. 11,432,717, which is further shown in enlarged views in FIGS. 8A-8B below. The endoscope 125 as shown in FIGS. 8A-8B has a rigid shaft 220 with a distal offset portion 222 that carries an image sensor 225. A large working channel 228 extends through the endoscope shaft 220.

FIG. 7 shows the resecting device 180 having an elongated shaft 252 introduced through the working channel 228 in the endoscope 125 with a distal rotating cutter 255 of the resecting device prepared to resect the fibroid 170 that is aligned with the axis of the cervical canal 172. The positioning of the cervical stabilizer 190 and the introduction, angulation, and rotation of the endoscope 125 are controlled by the controller 105 that operates the robotic arm 100A and the drive assembly 120 (FIGS. 1A-1B). Further, the axial movement, rotation, and actuation of cutter 255 of the resecting device 180 are controlled robotically by the controller 105 and drive assembly 120 (FIGS. 1A-1B). Contemporaneously, the ultrasound sensor or sensors 185 positioned on the serosa 166 of the uterus 128 (FIG. 5) send signals to the controller 105 to process and display ultrasound images on the display 116, which allows the physician to observe the resection procedure from both the intra-cavity endoscope 125 and the ultrasound images on the display 116. The controller 105 further is configured with mechanisms for stopping actuation of the resecting device 180, or for moving the resecting device 180 if the cutter 255 approaches or is within a selected distance from the serosa 166 of the uterus 128 to prevent perforation of the uterine wall. The controller 105 can also provide audio, visual or other warning signals to the physician to allow intervention to prevent the cutter 255 from perforating the uterine wall. In another variation, the endoscope images and ultrasound images can be overlaid or integrated to provide composite images of the targeted tissue in real time on the display 116.

Figure 5:
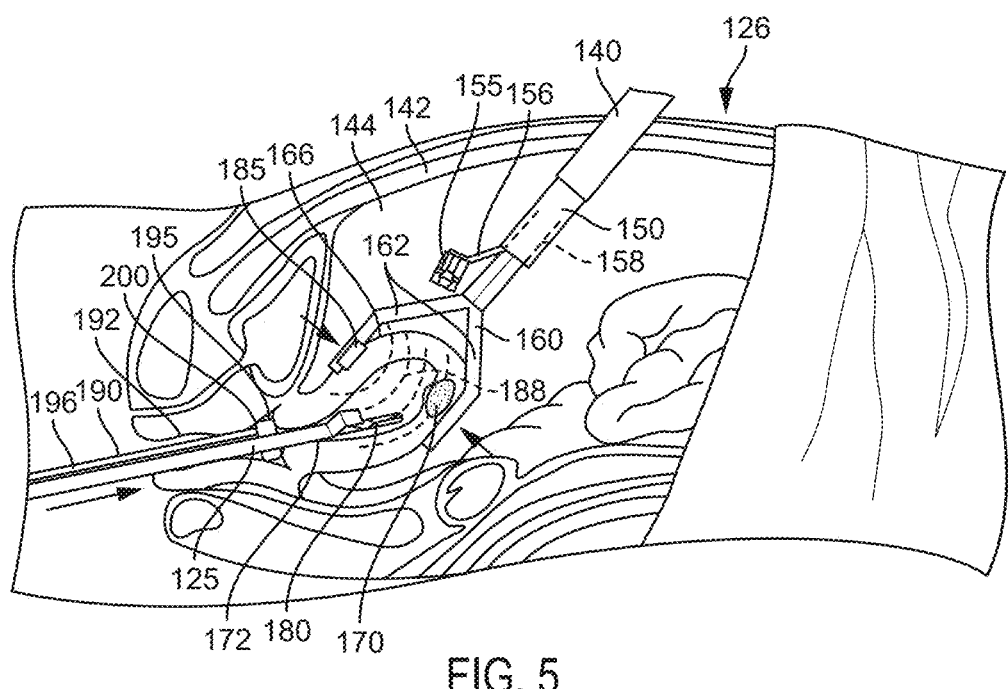
FIG. 5 illustrates a further step in the method where the laparoscopic grasping tool has mobilized the uterus such that a fibroid in the uterus is aligned with the patient's cervical canal, and further shows an ultrasound transducer carried by the grasper imaging the fibroid, and further showing the endoscope introduced into the uterine cavity with and a resecting device introduced through the working channel of the endoscope.

The use of an endoscope 125 and resecting device 180 of the type shown in FIGS. 5 and 7 is disclosed in more detail in the following commonly-owned patents and patent applications: U.S. Pat. Nos. 10,433,717, 11,259,695 and U.S. patent application Ser. Nos. 15/975,626; 16/351,909; 16/562,069; 16/848,050; 17/447,380 and 17/490,643.

Figures 10A, 10B:
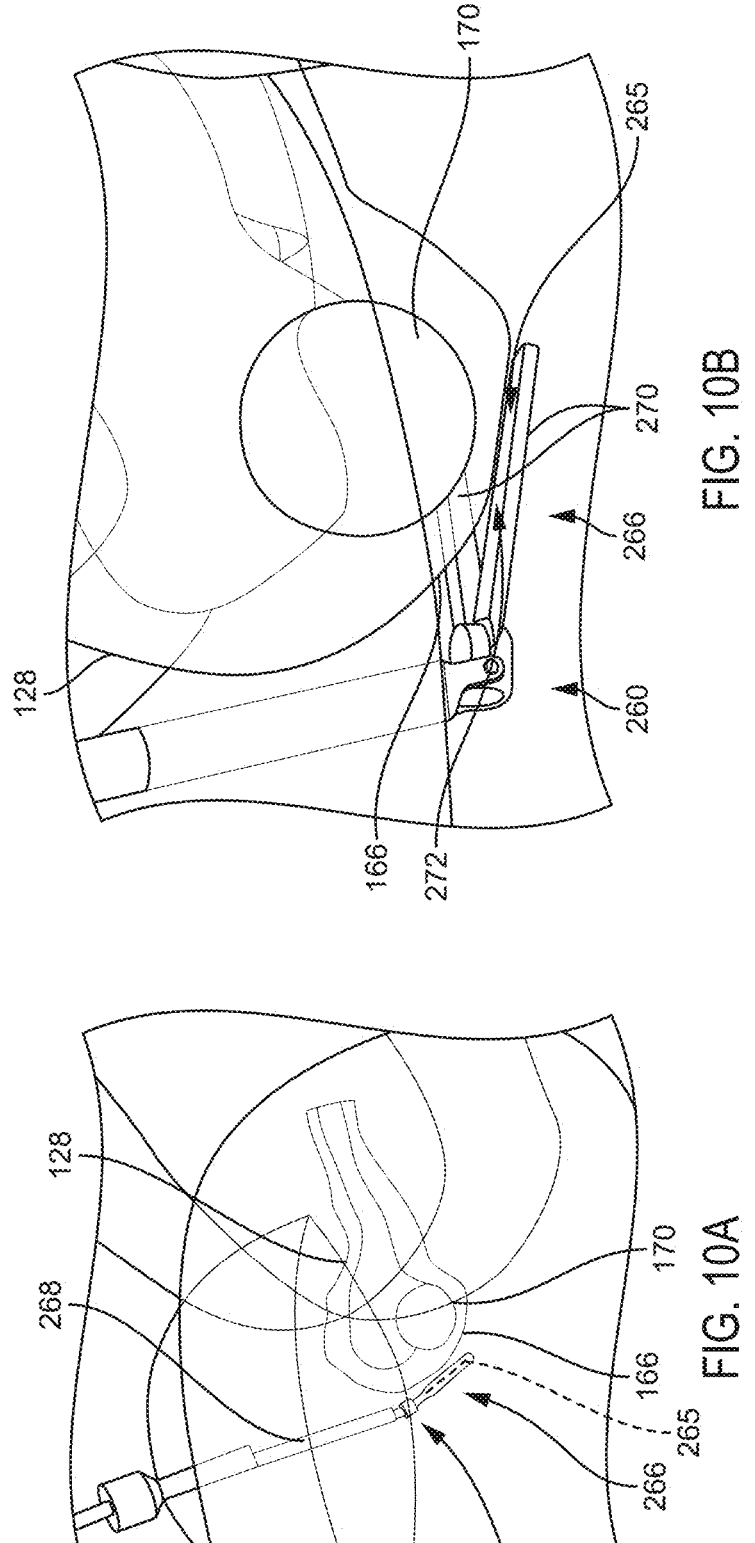
FIG. 10A is a schematic, transparent view of a patient's uterus and abdominal region showing laparoscopic access using another variation of a tool that carries at least one ultrasound transducer and a suction mechanism for engaging the exterior of the uterus.
FIG. 10B is an enlarged transparent view of a patient's uterus, from FIG. 10A showing articulation of the first and second arms of the tool to engage the ultrasound transducer (s) with the exterior of the uterus.

FIGS. 10A and 10B illustrate another form of laparoscopic tool 260, which carries ultrasound transducers 265 at a working end 266 thereof. In this variation, an elongated shaft 268 of the tool 260 extends through the working channel of an endoscope 150 and thereafter has first and second arms 270 that can be extended outwardly and angled relative to the shaft 268. In this variation, either or both of the articulating arms 270 (FIG. 10B) carry aspiration ports 272 for suctioning the serosa 166 of the uterus 128 against the ultrasound transducer(s) 265. Sensors can be provided to select and/or control the number of operating aspiration ports 272 to prevent excess evacuation of its inflation gas from the abdominal cavity. Once the arms 270 are suctioned into contact with the serosa 166, the tool 260 also can be used to manipulate and move the uterus 128 as described above to align the targeted tissue (e.g., a fibroid 170) with the patient's cervical canal 172 as described above. The ultrasound transducers 265 are configured to send signals to the controller 105 to process to display ultrasound images on the monitor 116 ad described previously.

Figure 11A:
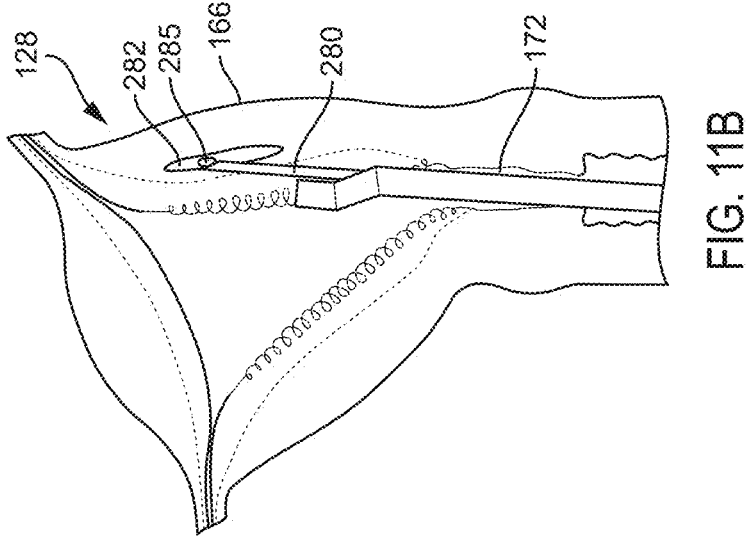
FIG. 11A is a schematic view of a patient's uterus showing another variation of a method of the invention where an endoscope and resecting device are introduced into the uterine wall to resect an intramural fibroid.
Figure 11B:
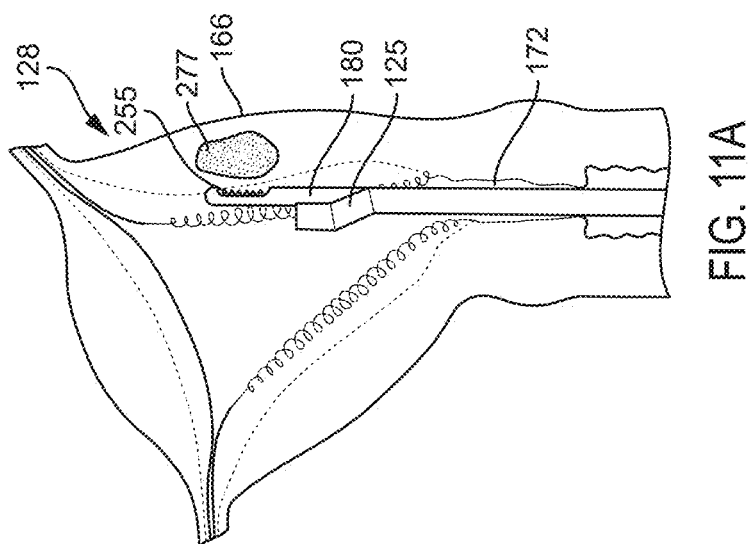
FIG. 11B is a subsequent step of the method of FIG. 11A, where the intramural fibroid has been resected, the resecting device has been withdrawn, and an injection device has been introduced through the working channel to deliver a tissue adhesive to the intramural space from which that fibroid has been removed.

FIGS. 11A and 11B show another variation of a method and device corresponding to the invention where an intramural fibroid 277 is resected. The method of resecting the fibroid 277 is the same as described above, except after the resecting device 180 may have a sharp distal tip (not shown) for penetrating into the wall of the uterus 128 to access the intramural fibroid 277. FIG. 11B shows another step of the method after the resecting device 180 has been removed from the site. Thereafter, an elongated injection tool 280 is introduced in the resected space 282, and a tissue adhesive 285 is injected into the space 282 from which the fibroid 277 has been removed. In this variation, the adhesive or glue 285 will bond the walls of the space 282 together, where the walls will be approximated by natural forces or by the physician using a tool to press on the interior of the uterine wall to compress the space 282. Suitable biocompatible tissue adhesives are known in the art. Variations of such glues and tissue adhesions are disclosed in the following article: Vrushali Bhagat, Matthew L. Becker; "Degradable Adhesives for Surgery and Tissue Engineering"; Biomacromolecules 2017-18 (10), 3009-3039.

Figure 12:
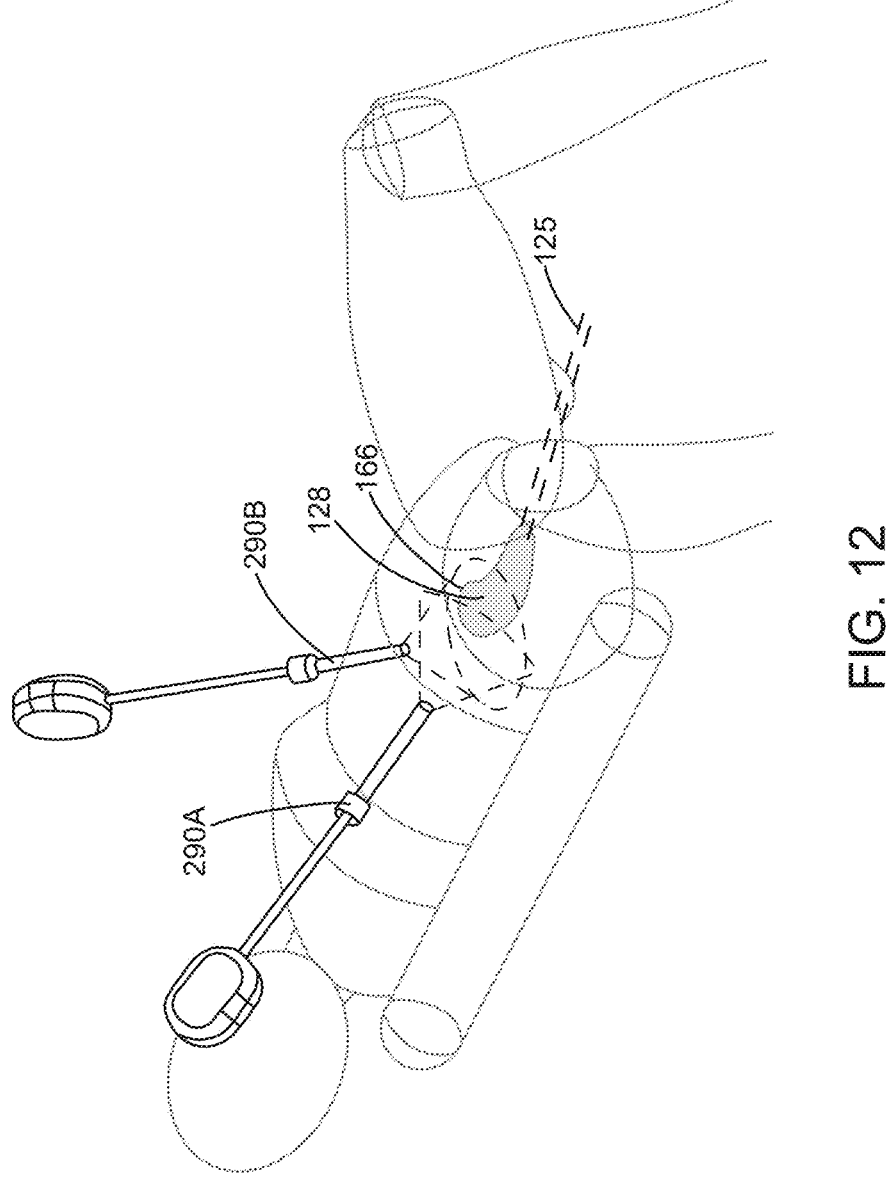
FIG. 12 shows another variation of a method of the invention with two laparoscopic arms introducing two tools into the patient's abdominal cavity from spaced apart ports.

FIG. 12 shows another variation of a method corresponding to the invention where two robotic arms with two laparoscopic ports, 290A and 290B, are used for laparoscopic access instead of a single laparoscopic access as described above. In this variation, tools introduced through one port can be adapted for viewing of the uterus 128 and manipulation of the uterus. Tools introduced through the second port can be used for positioning the ultrasound transducers against the serosa 166 of the patient's uterus 128. In this variation, the trans-cervical introduction of an endoscope 125 and resecting device 180 would perform as described above.

In another variation of, a uterine manipulation device (not shown) can be introduced trans-cervically. Such manipulation devices are known in the art and comprise an elongate member with an articulating joint or wrist within a region of the shaft, either in the uterine cavity or outside the cervix. Articulation of the working end can then reposition the uterus. Often, such devices have an expandable balloon at the working end of the elongated shaft. Such a uterine manipulation device can be introduced through an endoscope 125 as described above, or the manipulator can be used without an endoscope. In some variations, an endoscope can be introduced through the shaft of the manipulation device. In other variations, an endoscope and resecting device can be introduced through a working channel of the manipulation device. In some variations, the endoscope and resecting device can have flexible or articulating shafts to be used with an articulating manipulation device. The purpose of such manipulation devices again is to reposition the uterus such that the targeted tissue or fibroid is aligned with the cervical canal 172 of the patient to allow the straight-shaft resecting device to access the targeted tissue OK. Uterine manipulation devices that can be adapted for the methods above are shown in following patents and patent applications: U.S. Pat. Nos. 5,832,252; 10,695,092; 8,545,513; 10,881,432 and U.S. Patent Applications 2021/0361272 and 2012/0323079.

Although particular embodiments of the present invention have been described above in detail, it will be understood that this description is merely for purposes of illustration and the above description of the invention is not exhaustive. Specific features of the invention are shown in some drawings and not in others, and this is for convenience only, and any feature may be combined with another in accordance with the invention. A number of variations and alternatives will be apparent to one having ordinary skills in the art. Such alternatives and variations are intended to be included within the scope of the claims.

Particular features that are presented in dependent claims can be combined and fall within the scope of the invention. The invention also encompasses embodiments as if dependent claims were alternatively written in a multiple dependent claim format with reference to other independent claims.

It is important to note that, where possible, aspects of the various described embodiments or the embodiments themselves can be combined, where such combinations are intended to be within the scope of this disclosure. All references, including publications, patent applications, and patents, cited herein are hereby incorporated by reference to the same extent as if each reference were individually and specifically indicated to be incorporated by reference and were set forth in its entirety herein.

What is claimed is:

1. A method of treating a uterine disorder in a patient, comprising:

providing a medical system with a first arm and a second arm, each having a plurality of moveable arm segments;

positioning the first arm with a distal arm segment carrying an elongate tool introduced trans-vaginally to engage and stabilize a cervix of the patient;

positioning the second arm to laparoscopically introduce a tool assembly into an abdominal cavity of the patient wherein the tool assembly carries an image sensor and at least one ultrasound transducer, and positioning the at least one ultrasound transducer against a wall of a uterus for providing ultrasound images thereof;

introducing an elongate resecting device trans-cervically into a uterine cavity of the patient; and actuating the elongate resecting device to rotate and/or reciprocate a cutter carried at a distal end of the elongate resecting device to resect tissue at a targeted site contemporaneous with ultrasound imaging of the targeted site.

2. The method of claim 1 wherein the first arm is positioned robotically.

3. The method of claim 1 wherein the first arm is positioned manually.

4. The method of claim 1 wherein the second arm is positioned robotically.

5. The method of claim 1 wherein the second arm is positioned manually.

6. The method of claim 1 further comprising introducing an elongate manipulator trans-cervically into the uterine cavity and moving the elongate manipulator to align the targeted site with an axis of a cervical canal of the patient.

7. The method of claim 1 further comprising introducing an elongate endoscope trans-cervically into the uterine cavity.

8. The method of claim 1 further comprising robotically moving the cutter axially and/or angularly to resect a volume of tissue at the targeted site.

9. The method of claim 8 wherein the targeted site includes a fibroid.

10. The method of claim 8 wherein moving the cutter axially and/or angularly is responsive to signals from the at least one ultrasound transducer to control a location of the cutter.

* * * * *